US012390294B2

(12) United States Patent
Heiliger

(10) Patent No.: US 12,390,294 B2
(45) Date of Patent: Aug. 19, 2025

(54) ROBOTIC SURGICAL ASSEMBLIES INCLUDING SURGICAL INSTRUMENTS HAVING ARTICULATABLE WRIST ASSEMBLIES

(71) Applicant: Covidien LP, Mansfield, MA (US)

(72) Inventor: Zachary S. Heiliger, Nederland, CO (US)

(73) Assignee: Covidien LP, Mansfield, MA (US)

( * ) Notice: Subject to any disclaimer, the term of this patent is extended or adjusted under 35 U.S.C. 154(b) by 415 days.

(21) Appl. No.: 17/979,105

(22) Filed: Nov. 2, 2022

(65) Prior Publication Data

US 2023/0181274 A1 Jun. 15, 2023

Related U.S. Application Data

(60) Provisional application No. 63/289,361, filed on Dec. 14, 2021.

(51) Int. Cl.
*A61B 34/30* (2016.01)
*A61B 34/00* (2016.01)

(52) U.S. Cl.
CPC .............. *A61B 34/71* (2016.02); *A61B 34/70* (2016.02); *A61B 34/30* (2016.02)

(58) Field of Classification Search
CPC ......... A61B 34/71; A61B 34/70; A61B 34/30; A61B 2034/302; A61B 2034/303; A61B 2034/305; A61B 17/068; A61B 17/28; A61B 17/2804; A61B 17/29; A61B 17/00234; A61B 2017/0046; A61B 2017/00464; A61B 2017/00473; A61B 2017/00367; A61B 2017/00477
See application file for complete search history.

(56) References Cited

U.S. PATENT DOCUMENTS

| | | | |
|---|---|---|---|
| 6,132,368 A | 10/2000 | Cooper | |
| 6,206,903 B1 | 3/2001 | Ramans | |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |

(Continued)

OTHER PUBLICATIONS

Extended European Search Report dated May 3, 2023 for EP Applicaion No. 22213048.6, 12 pages.

*Primary Examiner* — Dianne Dornbusch
(74) *Attorney, Agent, or Firm* — Carter, DeLuca & Farrell LLP

(57) ABSTRACT

A surgical instrument for use in a robotic surgical system includes an end effector, a housing configured to be operably coupled to an instrument drive unit, a shaft extending distally from the housing, a wrist assembly coupled to a distal end portion of the shaft, articulation cables that adjust the pitch and yaw of the end effector relative to the shaft, and a differential gear mechanism that transfers an input rotation to the articulation cables.

20 Claims, 6 Drawing Sheets

(56) References Cited

U.S. PATENT DOCUMENTS

| | | |
|---|---|---|
| 6,659,939 B2 | 12/2003 | Moll |
| 6,671,581 B2 | 12/2003 | Niemeyer et al. |
| 6,676,684 B1 | 1/2004 | Morley et al. |
| 6,685,698 B2 | 2/2004 | Morley et al. |
| 6,699,235 B2 | 3/2004 | Wallace et al. |
| 6,714,839 B2 | 3/2004 | Salisbury, Jr. et al. |
| 6,716,233 B1 | 4/2004 | Whitman |
| 6,728,599 B2 | 4/2004 | Wang et al. |
| 6,746,443 B1 | 6/2004 | Morley et al. |
| 6,766,204 B2 | 7/2004 | Niemeyer et al. |
| 6,770,081 B1 | 8/2004 | Cooper et al. |
| 6,772,053 B2 | 8/2004 | Niemeyer |
| 6,783,524 B2 | 8/2004 | Anderson et al. |
| 6,793,652 B1 | 9/2004 | Whitman et al. |
| 6,793,653 B2 | 9/2004 | Sanchez et al. |
| 6,799,065 B1 | 9/2004 | Niemeyer |
| 6,837,883 B2 | 1/2005 | Moll et al. |
| 6,839,612 B2 | 1/2005 | Sanchez et al. |
| 6,840,938 B1 | 1/2005 | Morley et al. |
| 6,843,403 B2 | 1/2005 | Whitman |
| 6,846,309 B2 | 1/2005 | Whitman et al. |
| 6,866,671 B2 | 3/2005 | Tierney et al. |
| 6,871,117 B2 | 3/2005 | Wang et al. |
| 6,879,880 B2 | 4/2005 | Nowlin et al. |
| 6,899,705 B2 | 5/2005 | Niemeyer |
| 6,902,560 B1 | 6/2005 | Morley et al. |
| 6,936,042 B2 | 8/2005 | Wallace et al. |
| 6,951,535 B2 | 10/2005 | Ghodoussi et al. |
| 6,974,449 B2 | 12/2005 | Niemeyer |
| 6,991,627 B2 | 1/2006 | Madhani et al. |
| 6,994,708 B2 | 2/2006 | Manzo |
| 7,048,745 B2 | 5/2006 | Tierney et al. |
| 7,066,926 B2 | 6/2006 | Wallace et al. |
| 7,118,582 B1 | 10/2006 | Wang et al. |
| 7,125,403 B2 | 10/2006 | Julian et al. |
| 7,155,315 B2 | 12/2006 | Niemeyer et al. |
| 7,239,940 B2 | 7/2007 | Wang et al. |
| 7,306,597 B2 | 12/2007 | Manzo |
| 7,357,774 B2 | 4/2008 | Cooper |
| 7,373,219 B2 | 5/2008 | Nowlin et al. |
| 7,379,790 B2 | 5/2008 | Toth et al. |
| 7,386,365 B2 | 6/2008 | Nixon |
| 7,391,173 B2 | 6/2008 | Schena |
| 7,398,707 B2 | 7/2008 | Morley et al. |
| 7,413,565 B2 | 8/2008 | Wang et al. |
| 7,453,227 B2 | 11/2008 | Prisco et al. |
| 7,524,320 B2 | 4/2009 | Tierney et al. |
| 7,574,250 B2 | 8/2009 | Niemeyer |
| 7,594,912 B2 | 9/2009 | Cooper et al. |
| 7,607,440 B2 | 10/2009 | Coste-Maniere et al. |
| 7,666,191 B2 | 2/2010 | Orban, III et al. |
| 7,682,357 B2 | 3/2010 | Ghodoussi et al. |
| 7,689,320 B2 | 3/2010 | Prisco et al. |
| 7,695,481 B2 | 4/2010 | Wang et al. |
| 7,695,485 B2 | 4/2010 | Whitman et al. |
| 7,699,855 B2 | 4/2010 | Anderson et al. |
| 7,713,263 B2 | 5/2010 | Niemeyer |
| 7,725,214 B2 | 5/2010 | Diolaiti |
| 7,727,244 B2 | 6/2010 | Orban, III et al. |
| 7,741,802 B2 | 6/2010 | Prisco |
| 7,756,036 B2 | 7/2010 | Druke et al. |
| 7,757,028 B2 | 7/2010 | Druke et al. |
| 7,762,825 B2 | 7/2010 | Burbank et al. |
| 7,778,733 B2 | 8/2010 | Nowlin et al. |
| 7,803,151 B2 | 9/2010 | Whitman |
| 7,806,891 B2 | 10/2010 | Nowlin et al. |
| 7,819,859 B2 | 10/2010 | Prisco et al. |
| 7,819,885 B2 | 10/2010 | Cooper |
| 7,824,401 B2 | 11/2010 | Manzo et al. |
| 7,835,823 B2 | 11/2010 | Sillman et al. |
| 7,843,158 B2 | 11/2010 | Prisco |
| 7,865,266 B2 | 1/2011 | Moll et al. |
| 7,865,269 B2 | 1/2011 | Prisco et al. |
| 7,886,743 B2 | 2/2011 | Cooper et al. |
| 7,899,578 B2 | 3/2011 | Prisco et al. |
| 7,907,166 B2 | 3/2011 | Lamprecht et al. |
| 7,935,130 B2 | 5/2011 | Williams |
| 7,963,913 B2 | 6/2011 | Devengenzo et al. |
| 7,983,793 B2 | 7/2011 | Toth et al. |
| 8,002,767 B2 | 8/2011 | Sanchez |
| 8,004,229 B2 | 8/2011 | Nowlin et al. |
| 8,012,170 B2 | 9/2011 | Whitman et al. |
| 8,054,752 B2 | 11/2011 | Druke et al. |
| 8,062,288 B2 | 11/2011 | Cooper et al. |
| 8,079,950 B2 | 12/2011 | Stern et al. |
| 8,100,133 B2 | 1/2012 | Mintz et al. |
| 8,108,072 B2 | 1/2012 | Zhao et al. |
| 8,120,301 B2 | 2/2012 | Goldberg et al. |
| 8,142,447 B2 | 3/2012 | Cooper et al. |
| 8,147,503 B2 | 4/2012 | Zhao et al. |
| 8,151,661 B2 | 4/2012 | Schena et al. |
| 8,155,479 B2 | 4/2012 | Hoffman et al. |
| 8,182,469 B2 | 5/2012 | Anderson et al. |
| 8,202,278 B2 | 6/2012 | Orban, III et al. |
| 8,206,406 B2 | 6/2012 | Orban, III |
| 8,210,413 B2 | 7/2012 | Whitman et al. |
| 8,216,250 B2 | 7/2012 | Orban, III et al. |
| 8,220,468 B2 | 7/2012 | Cooper et al. |
| 8,256,319 B2 | 9/2012 | Cooper et al. |
| 8,285,517 B2 | 10/2012 | Sillman et al. |
| 8,315,720 B2 | 11/2012 | Mohr et al. |
| 8,335,590 B2 | 12/2012 | Costa et al. |
| 8,347,757 B2 | 1/2013 | Duval |
| 8,374,723 B2 | 2/2013 | Zhao et al. |
| 8,418,073 B2 | 4/2013 | Mohr et al. |
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |

(56) References Cited

U.S. PATENT DOCUMENTS

| | | |
|---|---|---|
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,675,354 B2 | 6/2017 | Weir et al. |
| 9,687,312 B2 | 6/2017 | Dachs et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Piolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |

(56) References Cited

U.S. PATENT DOCUMENTS

| | | |
|---|---|---|
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2014/0318288 A1 | 10/2014 | Lee |
| 2018/0055589 A1 | 3/2018 | Joseph et al. |
| 2019/0357989 A1 | 11/2019 | Brisson et al. |
| 2020/0038128 A1 | 2/2020 | Joseph et al. |
| 2020/0229833 A1 | 7/2020 | Vakharia et al. |
| 2020/0237455 A1* | 7/2020 | Anglese .................. A61B 34/30 |
| 2020/0261166 A1* | 8/2020 | Anglese ............. A61B 18/1442 |
| 2020/0261167 A1* | 8/2020 | Anglese .................. A61B 34/71 |
| 2023/0181274 A1* | 6/2023 | Heiliger .................. A61B 34/71 |
| | | 606/130 |

* cited by examiner

ROBOTIC SURGICAL ASSEMBLIES INCLUDING SURGICAL INSTRUMENTS HAVING ARTICULATABLE WRIST ASSEMBLIES

CROSS-REFERENCE TO RELATED APPLICATION

This application claims the benefit of and priority to U.S. Provisional Patent Application No. 63/289,361, filed Dec. 14, 2021, the entire contents of which are incorporated by reference herein.

BACKGROUND

Some surgical robotic systems include a console supporting a surgical robotic arm and a surgical instrument or at least one end effector (e.g., forceps or a grasping tool) mounted to the robotic arm. The robotic arm provides mechanical power to the surgical instrument for its operation and movement. Each robotic arm may include an instrument drive unit operatively connected to the surgical instrument and coupled to the robotic arm via a rail. In operation, the robotic arm is moved to a position over a patient and then guides the surgical instrument into a small incision via a surgical trocar or a natural orifice of a patient to position the end effector at a work site within the patient's body. The instrument drive unit drives a rotation of each corresponding driven member of the attached surgical instrument to perform a surgical treatment. The instrument drive unit may be configured to articulate the end effector in a plurality of directions to adjust its pitch and/or yaw within a surgical site, to open/close jaw members, and/or to fire features thereof.

SUMMARY

In accordance with an aspect of the disclosure, a surgical instrument of a surgical robotic system is provided and includes a housing, a first transmission disposed within the housing, a shaft extending distally from the housing, an end effector pivotably coupled to a distal end portion of the shaft, and first and second articulation cables. The first transmission includes a rotatable first input shaft, first and second output shafts configured to rotate in response to a rotation of the first input shaft, and a first differential gear mechanism operably coupling the first input shaft to the first and second output shafts and the first and second output shafts to one another. Each of the first and second articulation cables has a proximal end portion operably coupled to the respective first and second output shafts, and a distal end portion secured to the end effector. The first and second articulation cables move axially in opposing directions at a different rate from one another to articulate the end effector relative to the shaft in response to the rotation of the first input shaft.

In aspects, the first transmission may further include first and second articulation nuts operably coupled to the respective first and second output shafts. The articulation nuts mayb e configured to translate along the respective first and second output shafts in response to a rotation of the first and second output shafts. The articulation cables may be axially fixed to the respective first and second articulation nuts.

In aspects, the first differential gear mechanism may include a ring gear, first and second spider gears coupled to the ring gear, and first and second side axles. The ring gear may be operably coupled to the first input shaft such that the ring gear is configured to be rotated by the first input shaft.

The first and second spider gears may be configured to rotate about a respective axis thereof relative to the ring gear and with the ring gear around a rotation axis of the ring gear. The first side axle may be operably coupled to the first output shaft and the first and second spider gears, and the second side axle may be operably coupled to the second output shaft and the first and second spider gears.

In aspects, the first side axle may have opposing first and second gears. The first gear may be operably coupled to the first and second spider gears and the second gear may be operably coupled to the first output shaft.

In aspects, the second side axle may have opposing first and second gears. The first gear of the second side axle may be operably coupled to the first and second spider gears and the second gear of the second side axle may be operably coupled to the second output shaft.

In aspects, the first input shaft may have a pinion gear non-rotationally fixed to a distal end portion thereof. The pinion gear may be in meshing engagement with the ring gear.

In aspects, the ring gear may rotate about an axis that is perpendicular to a rotation axis of the first input shaft.

In aspects, the surgical instrument may further include a second transmission nested with or positioned adjacent the first transmission and supported in the housing. The second transmission may include a rotatable second input shaft, third and fourth output shafts configured to rotate in response to a rotation of the second input shaft, and a second differential gear mechanism operably coupling the second input shaft to the third and fourth output shafts and the third and fourth output shafts to one another.

In aspects, the surgical instrument may further include third and fourth articulation cables each having a proximal end portion operably coupled to the respective third and fourth output shafts, and a distal end portion secured to the end effector, such that the third and fourth articulation cables move axially in opposing directions at a different rate from one another to articulate the end effector relative to the shaft in response to the rotation of the second input shaft.

In aspects, the surgical instrument may further include a wrist assembly movably coupling the end effector to the distal end portion of the shaft. The wrist assembly may be configured to allow the end effector to articulate relative to the distal end portion of the shaft to adjust both a pitch and yaw of the end effector.

In aspects, the first transmission may be configured to change the pitch of the end effector, and the second transmission may be configured to change the yaw of the end effector.

In accordance with another aspect of the disclosure, a surgical robotic system is provided that includes a surgical robotic arm, an instrument drive unit configured to be supported on the surgical robotic arm, and a surgical instrument configured to be coupled to and driven by the instrument drive unit. The surgical instrument includes a housing configured to be attached to the instrument drive unit, a first transmission disposed within the housing, a shaft extending distally from the housing, an end effector pivotably coupled to a distal end portion of the shaft, and first and second articulation cables. The first transmission includes a rotatable first input shaft drivingly coupled to a corresponding drive shaft of the instrument drive unit, first and second output shafts configured to rotate in response to a rotation of the first input shaft, and a first differential gear mechanism operably coupling the first input shaft to the first and second output shafts and the first and second output shafts to one another. Each of the first and second articulation cables has a proximal end portion operably coupled to the respective first and second output shafts, and a distal end portion secured to the end effector, such that the first and second articulation cables move axially in opposing directions at a different rate from one another to adjust a pitch or a yaw of the end effector relative to the shaft in response to the rotation of the first input shaft.

In aspects, the surgical instrument may further include a second transmission nested with or positioned adjacent the first transmission and supported in the housing. The second transmission may further include a rotatable second input shaft, third and fourth output shafts configured to rotate in response to a rotation of the second input shaft, and a second differential gear mechanism operably coupling the second input shaft to the third and fourth output shafts and the third and fourth output shafts to one another. The surgical instrument may further include third and fourth articulation cables each having a proximal end portion operably coupled to the respective third and fourth output shafts, and a distal end portion secured to the end effector, such that the third and fourth articulation cables move axially in opposing directions at a different rate from one another to articulate the end effector relative to the shaft in response to the rotation of the second input shaft.

In aspects, the surgical instrument may further include a wrist assembly movably coupling the end effector to the distal end portion of the shaft. The wrist assembly may be configured to allow the end effector to articulate relative to the distal end portion of the shaft to adjust both the pitch and yaw of the end effector.

In aspects, the first transmission may be configured to change the pitch of the end effector, and the second transmission may be configured to change the yaw of the end effector.

In aspects, the first transmission may further include first and second articulation nuts operably coupled to the respective first and second output shafts and configured to translate therealong in response to a rotation of the respective first and second output shafts. The first and second articulation cables may be axially fixed to the respective first and second articulation nuts.

In accordance with further aspects of the disclosure, a surgical instrument of a surgical robotic system is provided that includes a housing, a first transmission disposed within the housing, a shaft extending distally from the housing, an end effector pivotably coupled to a distal end portion of the shaft, and first and second articulation cables. The first transmission includes a rotatable first input shaft, first and second outputs configured to rotate in response to a rotation of the first input shaft, and a first differential gear mechanism operably coupling the first input shaft to the first and second outputs and the first and second outputs to one another. The first and second articulation cables each have a proximal end portion operably coupled to the respective first and second outputs, and a distal end portion secured to the end effector. The first and second articulation cables move axially in opposing directions at a different rate from one another to change the pitch or yaw of the end effector relative to the shaft in response to the rotation of the first input shaft.

In aspects, each of the first and second outputs may include an articulation wheel configured to rotate via the first differential gear mechanism. The first and second articulation cables may be attached to the respective articulation wheels, such that the rotation of the articulation wheels axially moves the first and second articulation cables in the opposing directions.

In aspects, the first output may include a left-handed lead screw and the second output may include a right-handed lead screw.

In aspects, the first transmission may further include first and second articulation nuts operably coupled to the respective left-handed and right-handed lead screws. The articulation nuts may be configured to translate along the left-handed and right-handed lead screws in response to the rotation of the respective lead screws. The articulation cables may be axially fixed to the respective first and second articulation nuts.

In aspects, the surgical instrument may further include a second transmission nested with or positioned adjacent the first transmission and supported in the housing. The second transmission may include a rotatable second input shaft, third and fourth outputs configured to rotate in response to a rotation of the second input shaft, and a second differential gear mechanism operably coupling the second input shaft to the third and fourth outputs and the third and fourth outputs to one another. The surgical instrument may further include third and fourth articulation cables each having a proximal end portion operably coupled to the respective third and fourth output shafts, and a distal end portion secured to the end effector, such that the third and fourth articulation cables move axially in opposing directions at a different rate from one another to articulate the end effector relative to the shaft in response to the rotation of the second input shaft.

Further details and aspects of exemplary embodiments of the disclosure are described in more detail below with reference to the appended figures.

As used herein, the terms parallel and perpendicular are understood to include relative configurations that are substantially parallel and substantially perpendicular up to about + or −10 degrees from true parallel and true perpendicular.

BRIEF DESCRIPTION OF THE DRAWINGS

Embodiments of the disclosure are described herein with reference to the accompanying drawings, wherein.

DETAILED DESCRIPTION

Figure 1:
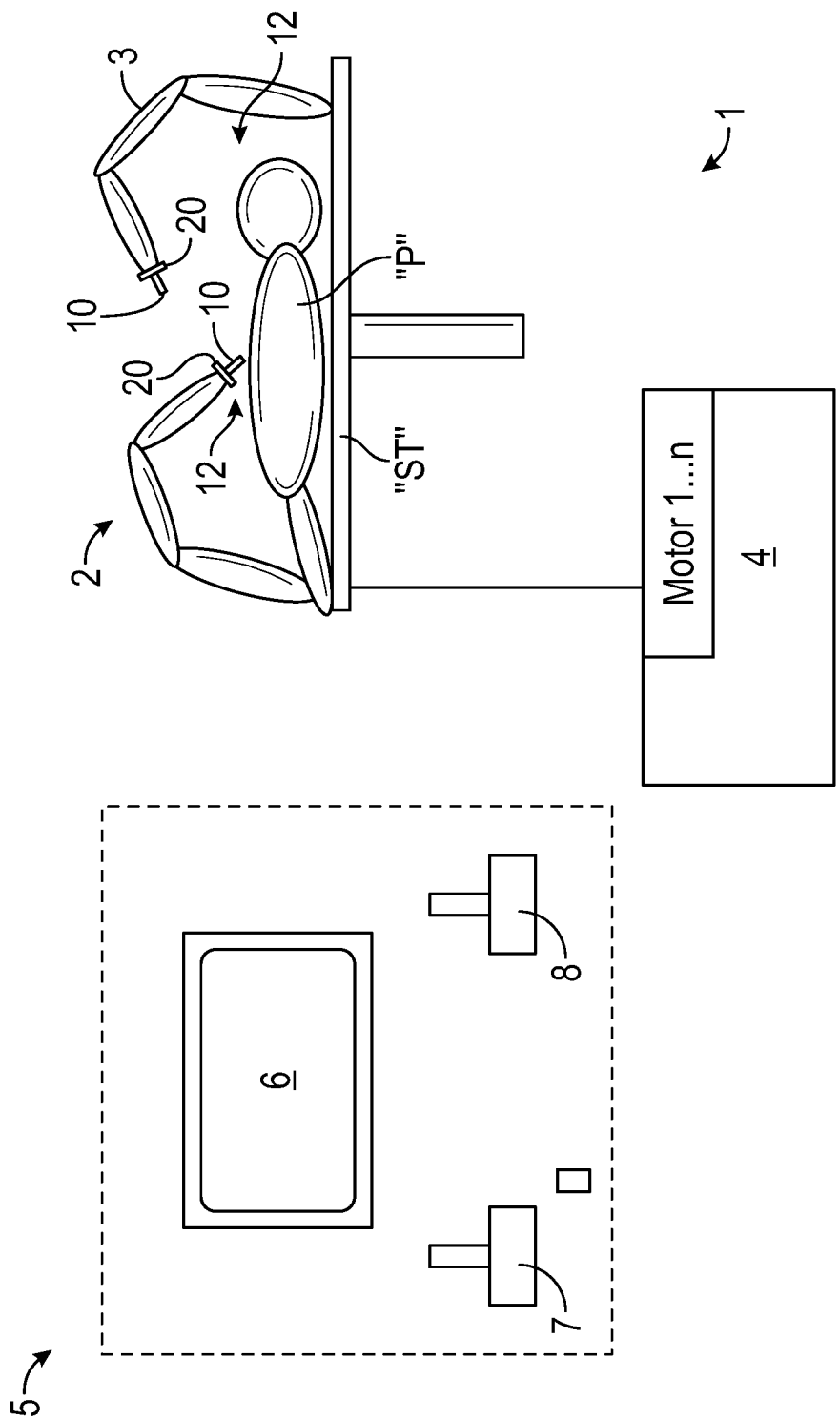
FIG. 1 is a schematic illustration of a robotic surgical system in accordance with the disclosure.

Embodiments of the disclosed robotic surgical system and methods thereof are described in detail with reference to the drawings, in which like reference numerals designate identical or corresponding elements in each of the several views. As used herein the term "distal" refers to that portion of the robotic surgical system or component thereof that is further from the user, while the term "proximal" refers to that portion of the robotic surgical system or component thereof that is closer to the user.

Articulation in a wristed robotic instrument is not linear. Stated differently, the wrist imposes a non-linear curve into the system. Consequently, an inside articulation cable is pulled back further than an outside articulation cable, therefore covering a greater axial distance in the same amount of time. Thus, because the two articulation cables are not driven the same distance during the same amount of time, the disclosure provides a differential. The differential converts rotational motion of an input shaft to rotational motion of two output axles. An open differential system allows for torque to be applied regardless of rotational differences between the output axles, covering variable distances in the same amount of time.

Figure 2:
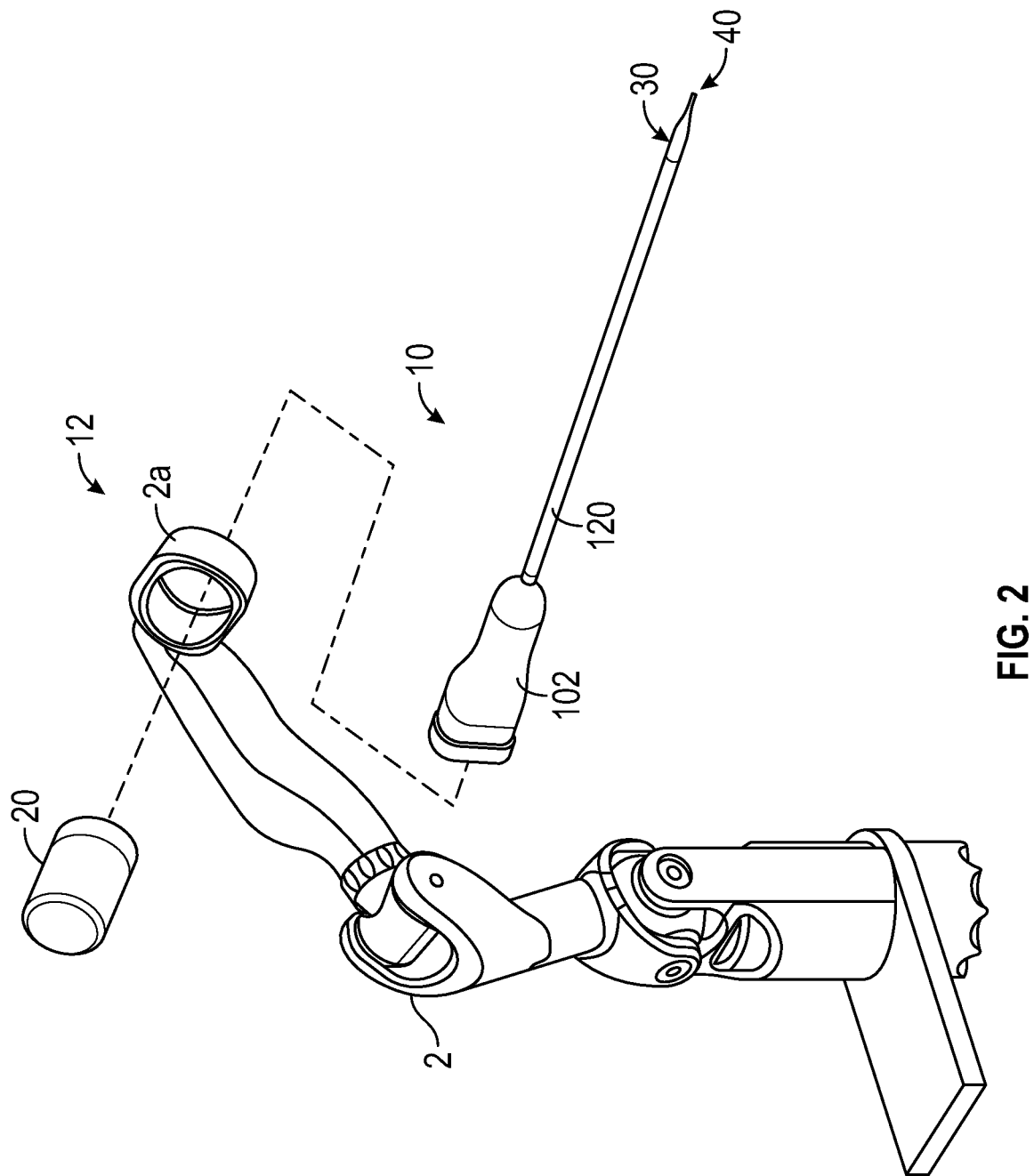
FIG. 2 is a perspective view of a surgical robotic arm of the robotic surgical system of FIG. 1 illustrating a surgical instrument and an instrument drive unit being coupled to the surgical robotic arm.

Referring initially to FIGS. 1 and 2, a robotic surgical system 1 is shown and generally includes a plurality of surgical robotic arms 2, 3 each having a surgical instrument 10 (e.g., an electrosurgical instrument, a surgical stapling instrument, a surgical forceps, or the like) removably coupled thereto; a control device 4 (e.g., a computer); and an operating console 5 coupled with the control device 4.

With continued reference to FIG. 1, the operating console 5 includes a display device 6, which is set up to display two-dimensional and three-dimensional images; and manual input devices 7, 8 that serve to enable a user (e.g., a surgeon) to telemanipulate robotic arms 2, 3, as known in principle to a person skilled in the art. Each of the robotic arms 2, 3 may include a plurality of members that are interconnected by joints. The robotic arms 2, 3 may be driven by electric drives (not shown) that are connected to the control device 4. The control device 4 is set up to execute a computer program to activate the electric drives in such a way that the robotic arms 2, 3, their instrument drive units 20, and thus the surgical instrument 10 execute a movement in accordance with a movement of the manual input devices 7, 8. The control device 4 may also be set up in such a way that it regulates the movement of the robotic arms 2, 3 and/or of the electric drives.

The robotic surgical system 1 is configured for minimally invasive treatment of a patient "P" lying on a surgical table "ST" using a surgical instrument (e.g., surgical instrument 10) coupled to the robotic surgical system 1. In some embodiments of the disclosure, the robotic surgical system 1 may include more than two robotic arms that are likewise coupled to the control device 4 and telemanipulatable by the operating console 5. A surgical instrument (e.g., surgical instrument 10) may also be attached to the additional robotic arm(s).

The surgical instrument 10 includes an end effector 40 (FIG. 2) for grasping and, in aspects, treating tissue. The control device 4 may control a plurality of motors (Motor 1 . . . n) with each motor configured to drive a relative rotation of drive members of a transmission assembly 100 (FIG. 3) of the surgical instrument 10 to effect operation and/or movement of the end effector 40 of the surgical instrument 10. It is contemplated that the control device 4 coordinates the activation of the various motors (Motor 1 . . . n) to coordinate a clockwise or counter-clockwise rotation of drive members (not shown) of the instrument drive unit 20 in order to coordinate an operation and/or movement of the end effector 40. In embodiments, each motor can be configured to actuate a drive rod or a lever arm to effect operation and/or movement of the end effector 40 of the surgical instrument 10.

With specific reference to FIG. 2, the robotic surgical system 1 includes a surgical assembly 12, which includes the robotic arm 2, the surgical instrument 10 coupled to the robotic arm 2, and the instrument drive unit 20 configured to operably couple to the surgical instrument 10. The instrument drive unit 20 is configured for powering the surgical instrument 10. The instrument drive unit 20 transfers power and actuation forces from its motors (not shown) to the transmission assembly 100 (FIG. 3) of the surgical instrument 10 to ultimately drive movement of components of the end effector 40, for example, a movement of a knife blade (not explicitly shown) for cutting tissue and a closing and opening of jaw members of the end effector 40 for grasping tissue, and/or drive an articulation of the end effector 40.

Figures 3, 4:
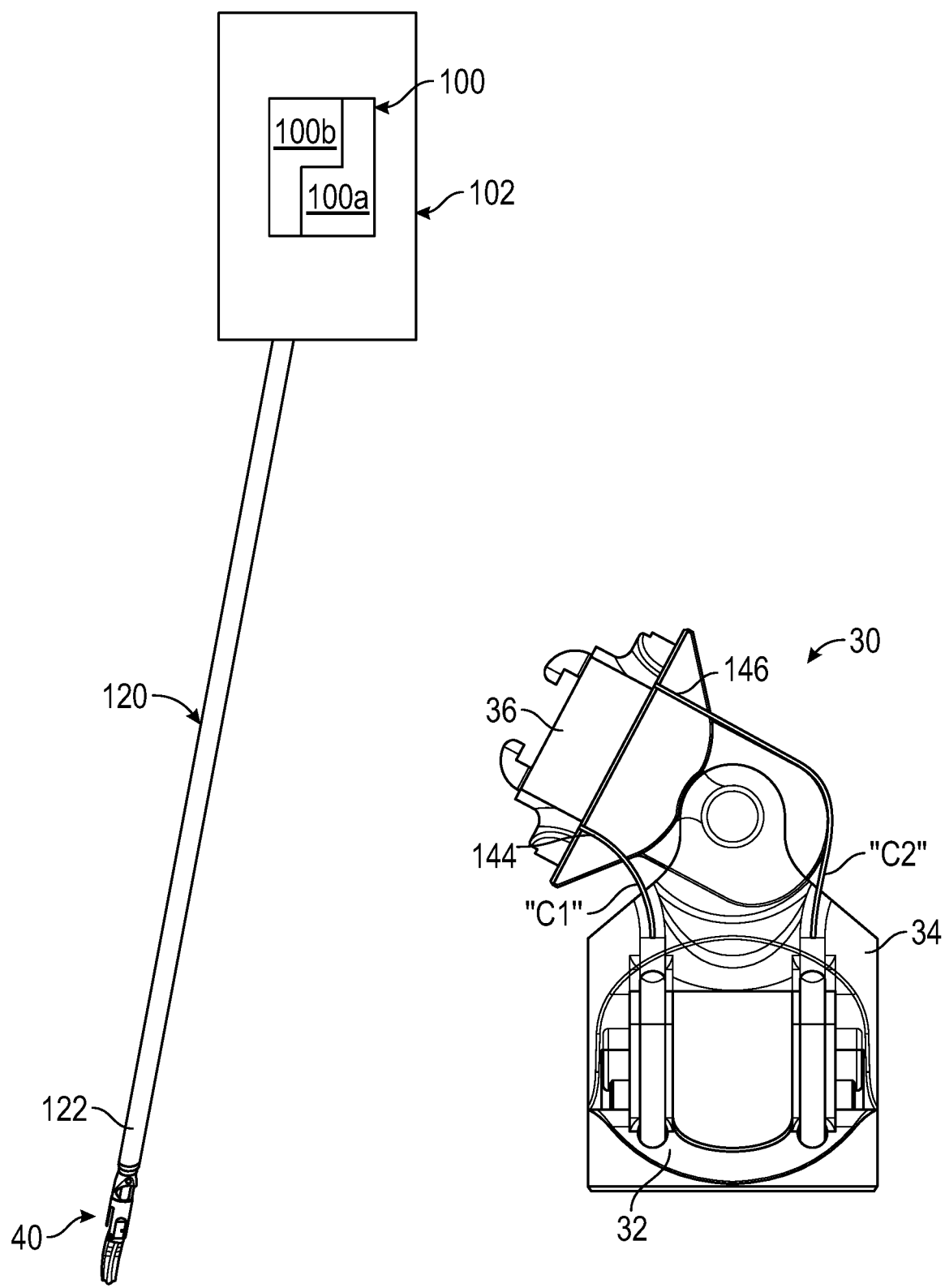
FIG. 3 is a perspective view, with parts shown schematically, of the surgical instrument of FIG. 2.
FIG. 4 is an enlarged, perspective view of a wrist assembly of the surgical instrument shown in FIG. 3.

With reference to FIGS. 2 and 3, the surgical instrument 10 generally includes a housing 102, a shaft 120 extending distally from the housing 102, and a wrist assembly 30 pivotably coupling the end effector 40 to the shaft 120. The housing 102 is configured to hook, latch, or otherwise attach to a surface of the robotic arm 2, e.g., the distal end 2a of the robotic arm 2, to secure the surgical instrument 10 to the robotic arm 2. In embodiments, the housing 102 may be attached to the surgical robotic arm 2 via various fastening engagements, such as, for example, clips, latches, friction fit engagement, buttons, a variety of fasteners, and/or a bayonet-type connection. The housing 102 houses the transmission assembly 100 that interfaces with the instrument drive unit 20. The transmission assembly 100 translates the motion and torques of the motors of the instrument drive unit 20 into the motion necessary to articulate the wrist assembly 30 of the surgical instrument 10, open and close the jaw members of the end effector 40, and deploy and retract a knife blade to cut tissue grasped between the jaw members of the end effector 40.

With brief reference to FIG. 4, the wrist assembly 30 of the surgical instrument 10 operably couples the end effector 40 to a distal end portion 122 (FIG. 3) of the shaft 120. More specifically, the wrist assembly 30 has a proximal body 32 immovably attached to the distal end portion 122 of the shaft 120, a proximal pivot member 34 pivotably coupled to the proximal body 32, and a distal pivot member 36 pivotably coupled to the proximal pivot member 34. The proximal pivot member 34 is pivotable about a first articulation axis relative to the proximal body 32 to adjust a pitch of the end effector 40, and the distal pivot member 36 is pivotable relative to the proximal pivot member 34 about a second articulation axis to adjust a yaw of the end effector 40. The wrist assembly 30 is configured to affect the pivoting motion of the end effector 40 relative to the shaft 120 to adjust the yaw and/or pitch of the end effector 40 utilizing a series of translatable cables driven by the motors of the instrument drive unit 20. One set of articulation cables "C1," "C2" for adjusting the yaw of the end effector 40 are routed through the wrist assembly 30 and fixed to the distal pivot member 36 of the wrist assembly 30 or a proximal end of the end effector 40. Accordingly, translation of selected cables pivots the end effector 40 in one of a plurality of directions, as will be described further below. The cables "C3," "C4" for effecting the change in pitch of the end effector 40 are shown in FIG. 5B.

Details about the transmission assembly 100 of the surgical instrument 10 will now be described with reference to FIGS. 3-5B. The transmission assembly 100 includes a first transmission 100a (FIG. 5A) and a second transmission 100b (FIG. 5B) each disposed within the housing 102 and nested with one another, or located in axial alignment with one another (e.g., first transmission 100a being located distal of second transmission 100b or first transmission 100a being located proximal of second transmission 100b).

The first transmission 100a includes a rotatable first input shaft 104, first and second output shafts 106, 108 each configured to rotate in response to a rotation of the first input shaft 104, and a first differential gear mechanism 110 operably coupling the first input shaft 104 to the first and second output shafts 106, 108 and the first and second output shafts 106, 108 to one another. The first input shaft 104 has a proximal end portion 104a configured to be drivingly coupled to a corresponding drive member or shaft (not shown) of the instrument drive unit 20 (FIG. 2), and a distal end portion having a pinion gear 104b non-rotationally fixed thereto. The pinion gear 104b is in meshing engagement with a ring gear 112 of the first differential gear mechanism 110 such that the ring gear 112 is rotatable by the pinion gear 104b of the first input shaft 104. The ring gear 112 rotates about an axis that is perpendicular to a rotation axis of the first input shaft 104. In aspects, the ring gear 112 may be a crown wheel.

In addition to the first differential gear mechanism 110 having the ring gear 112, the first differential gear mechanism 110 further includes first and second spider gears 114a, 114b coupled to the ring gear 112, and first and second side axles 116, 118 coupled to the respective spider gears 114a, 114b and the respective output shafts 106, 108. The spider gears 114a, 114b are rotatably supported on respective posts 120a, 120b that are fixed to the ring gear 112 and rotatable therewith about the rotation axis of the ring gear 112. As such, the first and second spider gears 114a, 114b are configured to rotate about their respective axes relative to the ring gear 112 and with the ring gear 112 around the rotation axis of the ring gear 112.

The first and second side axles 116, 118 of the first differential gear mechanism 110 each include opposing first and second gears 116a, 116b, 118a, 118b, such as, for example, bevel gears or crown gears. The first gear 116a of the first side axle 116 is in meshing engagement with both the first and second spider gears 114a, 114b and the second gear 116b of the first side axle 116 is in meshing engagement with a gear 124 (e.g., a bevel gear) of the first output shaft 106. The second side axle 118 extends through a central opening of the ring gear 112. The first gear 118a of the second side axle 118 is in meshing engagement with both the first and second spider gears 114a, 114b and the second gear 118b of the second side axle 118 is in meshing engagement with a gear 126 (e.g., a bevel gear) of the second output shaft 106. Due to the function of the first differential gear mechanism 110, the average of the rotational speed of the first and second output shafts 106, 108 is equal to the input rotational speed of the input drive shaft 104 such that an increase in the speed of one of the output shafts 106 or 108 results in a proportional decrease in the speed of the other of the output shafts 106, 108, the benefit of which will be described in further detail below.

Figure 5A:
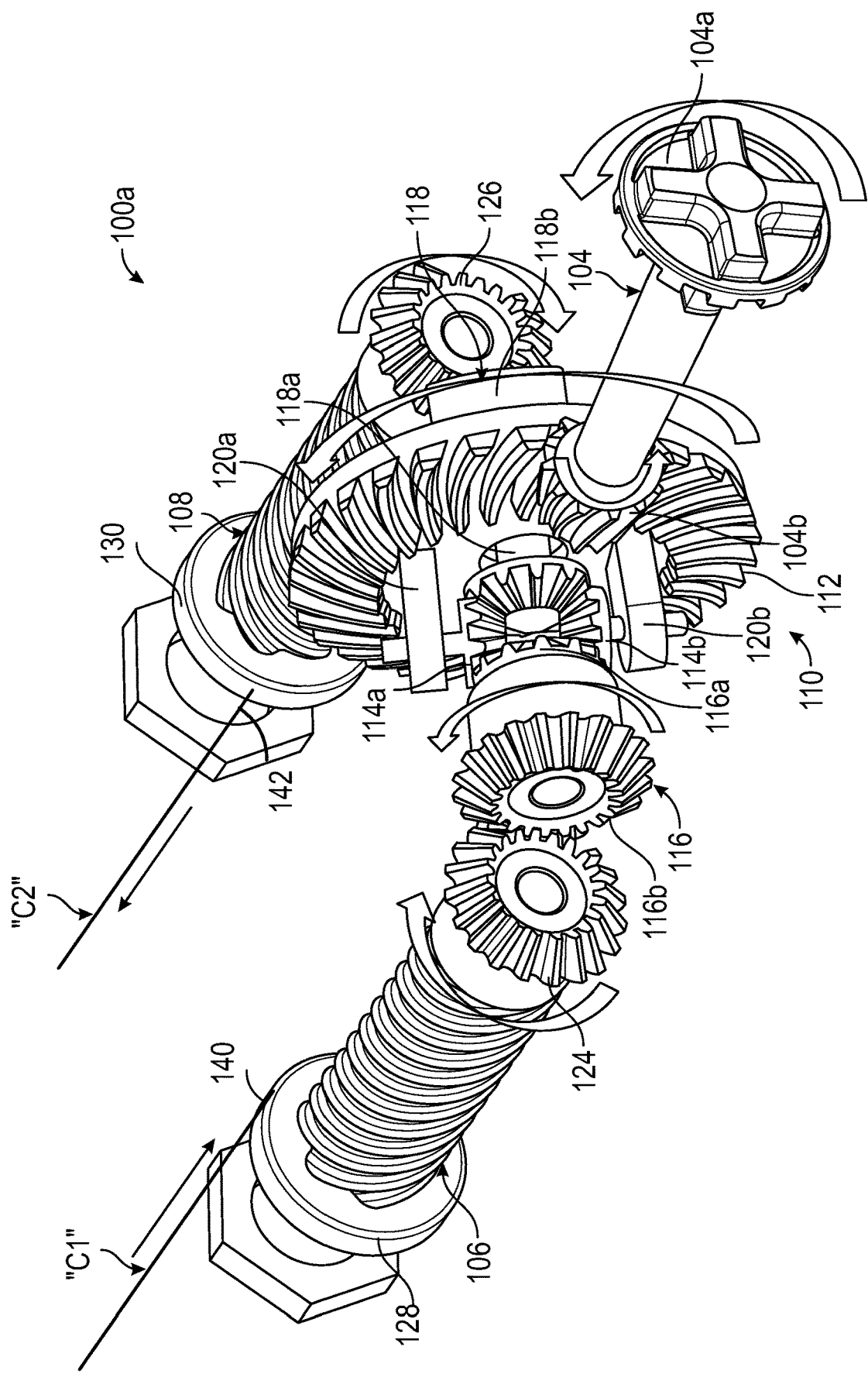
FIG. 5A is a perspective view illustrating a first transmission of the surgical instrument of FIG. 2.
Figure 5B:
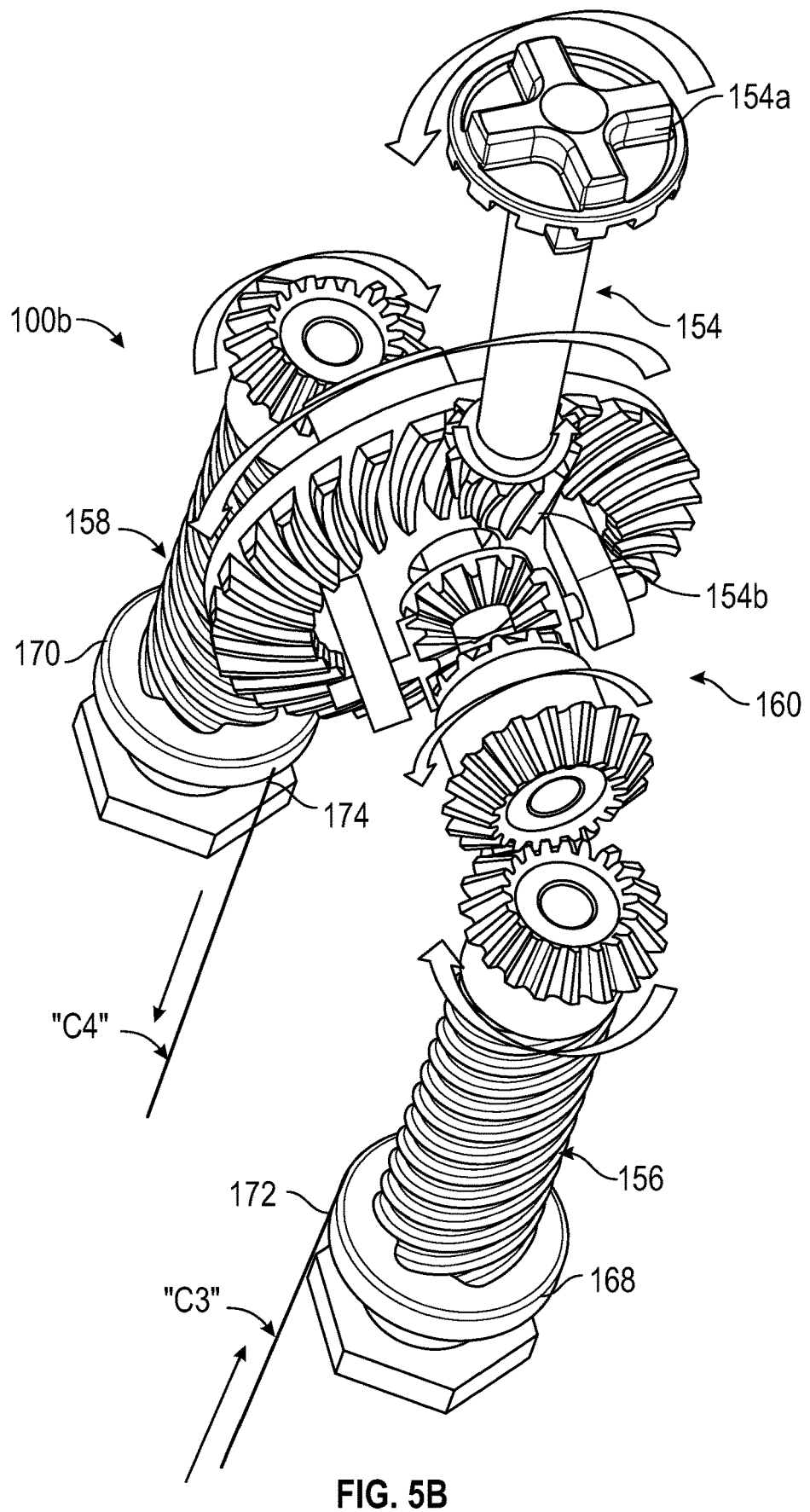
FIG. 5B is a perspective view illustrating a second transmission of the surgical instrument of FIG. 2.

With continued reference to FIG. 5A, the first transmission 100a further includes first and second articulation nuts 128, 130 operably coupled to the respective first and second output shafts 106, 108. The first output shaft 106 may be a left-handed lead screw and the second output shaft 108 may be a right-handed lead screw such that rotation of the output shafts 106, 108 in the same rotational direction is configured to translate the respective articulation nuts 128, 130 therealong in opposing axial directions. For example, as the output shafts 106, 108 rotate in a clockwise direction, the first articulation nut 128 may translate proximally whereas the second articulation nut 130 may translate distally. The first and second articulation cables "C 1," "C2" each have a proximal end portion 140, 142 operably coupled to the respective first and second output shafts 106, 108, and a distal end portion 144, 146 (FIG. 4) secured to the end effector 40, such that the first and second articulation cables "C1," "C2" move axially in opposing directions at a different rate from one another to articulate the end effector 40 relative to the shaft 120 to adjust a yaw of the end effector 40.

As illustrated in Table 1 below, it has been discovered that the degree of articulation of the end effector 40 is not linear to the degree of axial movement of the cables "C1-C4"; rather, articulation of the wrist assembly 30 imposes a non-linear curve into the system and to the degree of axial movement of the cables "C1-C4". Consequently, the inside articulation cable (e.g., articulation cable "C1") is translated proximally a greater distance than the outside articulation cable (e.g., articulation cable "C2") is translated distally. That is, the inside articulation cable "C1" traverses a greater axial distance in the same amount of time than does the outside articulation cable "C2". The differential gear mechanism 110 compensates for this difference to allow for the inside articulation cable "C1" to traverse the greater axial distance in the same amount of time thereby reducing stress and strain on the inside articulation cable "C2". Therefore, use of the transmission assembly 100 of this disclosure will result in the articulation cables having a longer lifespan, and articulation of the end effector 40 will be more precise.

TABLE 1

| Joint Angle (deg) | Inside Cable (mm) | Outside Cable (mm) | Average Length (mm) | % Change |
| --- | --- | --- | --- | --- |
| 0 | 7.21313 | 7.21313 | 7.21313 | 0 |
| 15.5 | 6.52968 | 7.85589 | 7.192785 | −0.282852887 |
| 31 | 5.74358 | 8.63665 | 7.190115 | −0.320092238 |
| 46.5 | 4.88954 | 9.46854 | 7.17904 | −0.474854577 |
| 62 | 4.05633 | 10.3072 | 7.181765 | −0.436731082 |

With reference to FIG. 5B, the second transmission 100b (FIG. 5B) of the transmission assembly 100 is substantially similar or identical to the first transmission 100a but is configured to effect a change in pitch of the end effector 40 via translation of a second set of articulation cables "C3," "C4." The second transmission 100b is disposed within the housing 102 (FIG. 3) and may be orientated generally perpendicular to and nested with the first transmission 100a. In aspects, instead of nesting or overlapping the first and second transmissions 100a, 100b, the first and second transmissions 100a, 100b may be positioned in side-by-side relation to one another, or, as mentioned above, may be positioned distal/proximal to one another.

The second transmission 100b includes a rotatable first input shaft 154, first and second output shafts 156, 158 each configured to rotate in response to a rotation of the first input shaft 154, and a second differential gear mechanism 160 operably coupling the first input shaft 154 to the first and second output shafts 156, 158 and the first and second output shafts 156, 158 to one another. The first input shaft 154 has a proximal end portion 154a configured to be drivingly coupled to a corresponding drive member or shaft (not shown) of the instrument drive unit 20 (FIG. 2), and a distal end portion 154b operably coupled to the second differential gear mechanism 160. Since the second differential gear mechanism 160 is substantially similar or identical to the first differential gear mechanism 110, details of the second differential gear mechanism 160 are not provided herein.

The second transmission 100b further includes third and fourth articulation nuts 168, 170 operably coupled to the respective first and second output shafts 156, 158. The first output shaft 156 may be a left-handed lead screw and the second output shaft 158 may be a right-handed lead screw such that rotation of the output shafts 156, 158 in the same rotational direction is configured to translate the respective articulation nuts 168, 170 therealong in opposing axial directions. The articulation cables "C3," "C4" each have a proximal end portion 172, 174 operably coupled to the respective first and second output shafts 156, 158, and a distal end portion (not explicitly shown) secured to the end effector 40, such that the articulation cables "C3," "C4" move axially in opposing directions at a different rate from one another to articulate the end effector 40 relative to the shaft 120 to adjust a pitch of the end effector 40.

Figure 6:
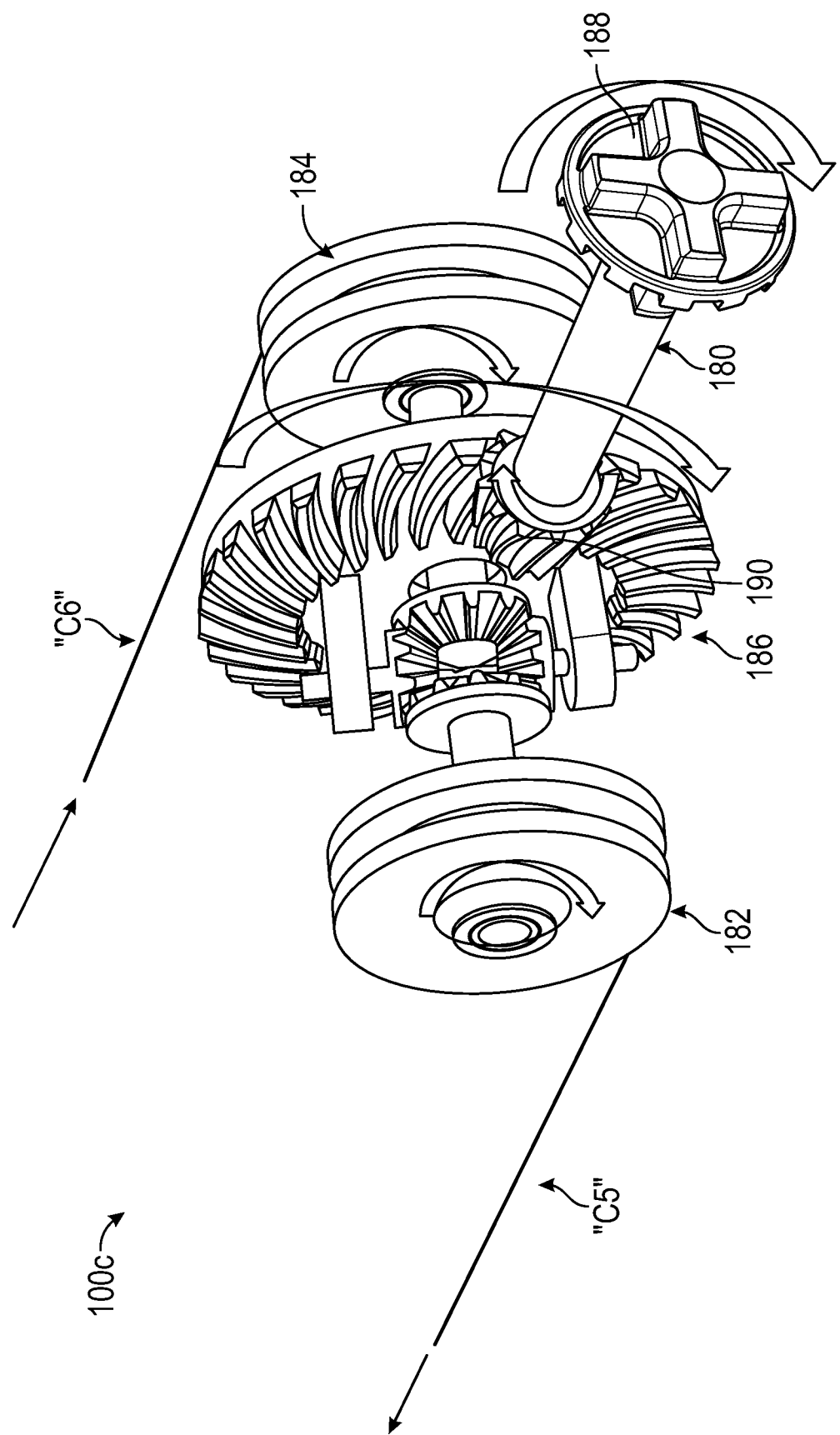
FIG. 6 is a perspective view illustrating a third transmission of the surgical instrument of the robotic surgical system of FIG. 2.

With reference to FIG. 6, another type of transmission 100c is illustrated that can be used in place of or in addition to one or both of the first and second transmissions 100a, 100b. Since the transmission 100c is substantially similar to transmissions 100a, 100b, only those details about the transmission 100c necessary to appreciate the differences from transmissions 100a, 100b will be provided.

The transmission 100c includes a rotatable first input shaft 180, first and second outputs 182, 184 each configured to rotate in response to a rotation of the first input shaft 180, and a third differential gear mechanism 186 operably coupling the first input shaft 180 to the first and second outputs 182, 184 and the first and second outputs 182, 184 to one another. The first input shaft 180 has a proximal end portion 188 configured to be drivingly coupled to a corresponding drive member or shaft (not shown) of the instrument drive unit 20 (FIG. 2), and a distal end portion 190 operably coupled to the third differential gear mechanism 186. Since the third differential gear mechanism 186 is substantially similar or identical to the first and second differential gear mechanisms 110, 160 described above, details of the third differential gear mechanism 180 are not provided herein.

The first and second outputs 182, 184 of the third transmission 100c may be an articulation wheel rotatably supported in the housing 102 and configured to rotate via the third differential gear mechanism 186. Articulation cables "C5," "C6" are fixed to the respective articulation wheels 182, 184 such that the rotation of the articulation wheels 182, 184 axially moves the first and second articulation cables "C5," "C6" in the opposing directions. For example, the articulation cables "C5," "C6" may be secured to the wheels 182, 184 by being wrapped about the wheels 182, 184 in opposing circumferential directions from one another such that rotation of the wheels 182, 184 in the same rotational direction results in the translation of the cables "C5," "C6" in opposing axial directions. In aspects, the outputs 182, 184 may be configured similarly to a capstan or a windlass.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. A surgical instrument of a surgical robotic system, the surgical instrument comprising:
    a housing;
    a first transmission disposed within the housing and including:
        a rotatable first input shaft;
        first and second output shafts configured to rotate in response to a rotation of the first input shaft; and
        a first differential gear mechanism operably coupling the first input shaft to the first and second output shafts and the first and second output shafts to one another;
    a shaft extending distally from the housing;
    an end effector pivotably coupled to a distal end portion of the shaft; and
    first and second articulation cables each having a proximal end portion operably coupled to the respective first and second output shafts, and a distal end portion secured to the end effector, such that the first and second articulation cables move axially in opposing directions at a different rate from one another to articulate the end effector relative to the shaft in response to the rotation of the first input shaft.

2. The surgical instrument according to claim 1, wherein the first transmission further includes first and second articulation nuts operably coupled to the respective first and second output shafts and configured to translate therealong in response to a rotation of the respective first and second output shafts, the first and second articulation cables being axially fixed to the respective first and second articulation nuts.

3. The surgical instrument according to claim 1, wherein the first differential gear mechanism includes:
    a ring gear operably coupled to the first input shaft such that the ring gear is configured to be rotated by the first input shaft;
    first and second spider gears coupled to the ring gear such that the first and second spider gears are configured to rotate about a respective axis thereof relative to the ring gear and with the ring gear around a rotation axis of the ring gear; and
    first and second side axles, the first side axle operably coupled to the first output shaft and the first and second spider gears, and the second side axle operably coupled to the second output shaft and the first and second spider gears.

4. The surgical instrument according to claim 3, wherein the first side axle has opposing first and second gears, the first gear is operably coupled to the first and second spider gears and the second gear is operably coupled to the first output shaft.

5. The surgical instrument according to claim 4, wherein the second side axle has opposing first and second gears, the first gear of the second side axle is operably coupled to the first and second spider gears and the second gear of the second side axle is operably coupled to the second output shaft.

6. The surgical instrument according to claim 3, wherein the first input shaft has a pinion gear non-rotationally fixed to a distal end portion thereof, the pinion gear being in meshing engagement with the ring gear.

7. The surgical instrument according to claim 3, wherein the ring gear rotates about an axis that is perpendicular to a rotation axis of the first input shaft.

8. The surgical instrument according to claim 1, further comprising:
    a second transmission nested with or positioned adjacent the first transmission and supported in the housing, wherein the second transmission includes:
        a rotatable second input shaft;
        third and fourth output shafts configured to rotate in response to a rotation of the second input shaft; and a second differential gear mechanism operably coupling the second input shaft to the third and fourth output shafts and the third and fourth output shafts to one another; and third and fourth articulation cables each having a proximal end portion operably coupled to the respective third and fourth output shafts, and a distal end portion secured to the end effector, such that the third and fourth articulation cables move axially in opposing directions at a different rate from one another to articulate the end effector relative to the shaft in response to the rotation of the second input shaft.

9. The surgical instrument according to claim 8, further comprising a wrist assembly movably coupling the end effector to the distal end portion of the shaft, wherein the wrist assembly is configured to allow the end effector to articulate relative to the distal end portion of the shaft to adjust both a pitch and yaw of the end effector.

10. The surgical instrument according to claim 9, wherein the first transmission is configured to change the pitch of the end effector, and the second transmission is configured to change the yaw of the end effector.

11. A surgical robotic system, comprising:
a surgical robotic arm;
an instrument drive unit configured to be supported on the surgical robotic arm; and
a surgical instrument configured to be coupled to and driven by the instrument drive unit, the surgical instrument including;
a housing configured to be attached to the instrument drive unit;
a first transmission disposed within the housing and including:
a rotatable first input shaft drivingly coupled to a corresponding drive shaft of the instrument drive unit;
first and second output shafts configured to rotate in response to a rotation of the first input shaft; and
a first differential gear mechanism operably coupling the first input shaft to the first and second output shafts and the first and second output shafts to one another;
a shaft extending distally from the housing;
an end effector pivotably coupled to a distal end portion of the shaft; and
first and second articulation cables each having a proximal end portion operably coupled to the respective first and second output shafts, and a distal end portion secured to the end effector, such that the first and second articulation cables move axially in opposing directions at a different rate from one another to adjust a pitch or a yaw of the end effector relative to the shaft in response to the rotation of the first input shaft.

12. The surgical robotic system according to claim 11, wherein the surgical instrument further includes:
a second transmission nested with or positioned adjacent the first transmission and supported in the housing, wherein the second transmission includes:
a rotatable second input shaft;
third and fourth output shafts configured to rotate in response to a rotation of the second input shaft; and
a second differential gear mechanism operably coupling the second input shaft to the third and fourth output shafts and the third and fourth output shafts to one another; and third and fourth articulation cables each having a proximal end portion operably coupled to the respective third and fourth output shafts, and a distal end portion secured to the end effector, such that the third and fourth articulation cables move axially in opposing directions at a different rate from one another to articulate the end effector relative to the shaft in response to the rotation of the second input shaft.

13. The surgical robotic system according to claim 12, wherein the surgical instrument further includes a wrist assembly movably coupling the end effector to the distal end portion of the shaft, wherein the wrist assembly is configured to allow the end effector to articulate relative to the distal end portion of the shaft to adjust both the pitch and yaw of the end effector.

14. The surgical robotic system according to claim 12, wherein the first transmission is configured to change the pitch of the end effector, and the second transmission is configured to change the yaw of the end effector.

15. The surgical robotic system according to claim 11, wherein the first transmission further includes first and second articulation nuts operably coupled to the respective first and second output shafts and configured to translate therealong in response to a rotation of the respective first and second output shafts, the first and second articulation cables being axially fixed to the respective first and second articulation nuts.

16. A surgical instrument of a surgical robotic system, the surgical instrument comprising:
a housing;
a first transmission disposed within the housing and including:
a rotatable first input shaft;
first and second outputs configured to rotate in response to a rotation of the first input shaft; and
a first differential gear mechanism operably coupling the first input shaft to the first and second outputs and the first and second outputs to one another;
a shaft extending distally from the housing;
an end effector pivotably coupled to a distal end portion of the shaft; and
first and second articulation cables each having a proximal end portion operably coupled to the respective first and second outputs, and a distal end portion secured to the end effector, such that the first and second articulation cables move axially in opposing directions at a different rate from one another to change the pitch or yaw of the end effector relative to the shaft in response to the rotation of the first input shaft.

17. The surgical instrument according to claim 16, wherein each of the first and second outputs includes an articulation wheel configured to rotate via the first differential gear mechanism, the first and second articulation cables being attached to the respective articulation wheels, such that the rotation of the articulation wheels axially moves the first and second articulation cables in the opposing directions.

18. The surgical instrument according to claim 16, wherein the first output includes a left-handed lead screw and the second output includes a right-handed lead screw.

19. The surgical instrument according to claim 18, wherein the first transmission further includes first and second articulation nuts operably coupled to the respective left-handed and right-handed lead screws and configured to translate therealong in response to the rotation of the respective left-handed and right-handed lead screws, the first and second articulation cables being axially fixed to the respective first and second articulation nuts.

20. The surgical instrument according to claim 16, further comprising:
- a second transmission nested with or positioned adjacent the first transmission and supported in the housing, wherein the second transmission includes:
  - a rotatable second input shaft;
  - third and fourth outputs configured to rotate in response to a rotation of the second input shaft; and
  - a second differential gear mechanism operably coupling the second input shaft to the third and fourth outputs and the third and fourth outputs to one another; and
- third and fourth articulation cables each having a proximal end portion operably coupled to the respective third and fourth outputs, and a distal end portion secured to the end effector, such that the third and fourth articulation cables move axially in opposing directions at a different rate from one another to articulate the end effector relative to the shaft in response to the rotation of the second input shaft.

\* \* \* \* \*